United States Patent [19]

Burgin

[11] Patent Number: 4,566,439

[45] Date of Patent: Jan. 28, 1986

[54] ACRYLOOPTIC EXAMINATION DEVICE WITH AUXILIARY LIGHT

[76] Inventor: Kermit H. Burgin, P.O. Box 334, Whitestown, Ind. 46075

[21] Appl. No.: 631,240

[22] Filed: Jul. 16, 1984

[51] Int. Cl.$^4$ ............................................... A61B 1/06
[52] U.S. Cl. .......................................... 128/6; 128/11; 128/18; 128/23
[58] Field of Search ................... 128/6, 11, 13, 16, 18, 128/22, 20, 23

[56] References Cited

U.S. PATENT DOCUMENTS

| | | | |
|---|---|---|---|
| 2,247,258 | 6/1941 | Shepard | 128/16 |
| 2,482,971 | 9/1949 | Golson | 128/6 |
| 2,690,745 | 10/1954 | Govan | 128/15 |
| 3,130,690 | 4/1964 | Johnston | 410/144 |
| 3,131,690 | 5/1964 | Innis et al. | 128/23 |
| 3,324,850 | 6/1967 | Gunning et al. | 128/18 |
| 3,592,199 | 7/1971 | Ostensen | 128/6 |
| 3,664,330 | 5/1972 | Deutsch | 128/18 |
| 3,716,047 | 2/1973 | Moore et al. | 128/18 |
| 3,762,400 | 10/1973 | McDonald | 128/18 |
| 3,796,214 | 3/1974 | Davis | 128/20 |
| 3,851,642 | 12/1974 | McDonald | 128/18 |
| 3,890,960 | 6/1975 | Wunsch et al. | 128/16 |
| 3,890,961 | 6/1975 | Moore et al. | 128/17 |
| 3,916,881 | 11/1975 | Heine | 128/16 |
| 3,978,850 | 9/1976 | Moore et al. | 128/9 |
| 4,086,919 | 5/1978 | Bullard | 128/11 |
| 4,156,424 | 5/1979 | Burgin | 128/18 |
| 4,165,746 | 8/1979 | Burgin | 128/18 X |
| 4,263,889 | 4/1981 | Martenson | 126/123 |
| 4,263,899 | 4/1981 | Burgin | 128/18 |

FOREIGN PATENT DOCUMENTS

| | | |
|---|---|---|
| 2302614 | 7/1974 | Fed. Rep. of Germany . |
| 25040 | of 1913 | United Kingdom ................. 128/18 |

*Primary Examiner*—William H. Grieb
*Attorney, Agent, or Firm*—Barnes & Thornburg

[57] ABSTRACT

An examination device including an examination head, a base unit having a handle portion and a head portion, a first stationary light source mounted in the head portion for providing light in and around the examination head, and a second light source movably mounted above the first light source.

8 Claims, 3 Drawing Figures

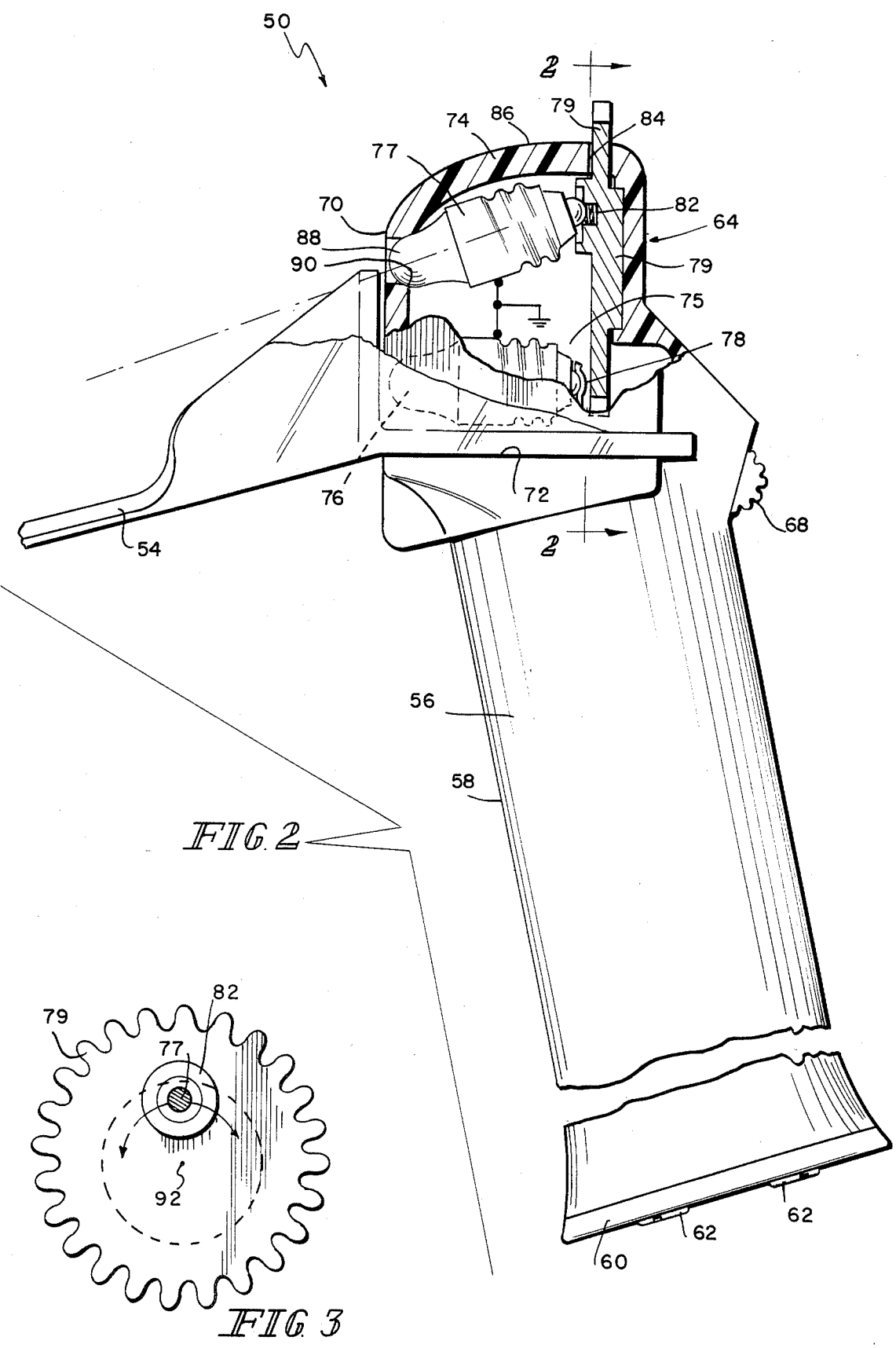

ACRYLOOPTIC EXAMINATION DEVICE WITH AUXILIARY LIGHT

This application relates to acrylooptic examination devices, and particularly to such devices in which the field upon which the device is to be used is to be illuminated by said device.

A number of medical instruments utilizing fiber optic or acrylooptic characteristics are known. These include, by way of example, the devices described and illustrated in the following U.S. Pat. Nos.: 3,644,330; 3,762,400; 3,796,214; 3,716,047; 3,890,961; 2,247,258; 4,086,919; 3,851,642; 3,592,199; 3,324,850; 3,131,691; 2,482,971; 3,978,850; 2,690,745; 3,890,961; 3,916,881; 4,165,746; 4,263,899; and 4,156,424. There is also a device illustrated in German Offenlegungsschrift No. 2,302,614.

Each of these previous devices has utilized a single source of illumination to supply light to a field being observed. This form of illumination has proven to be unsatisfactory when an operator has wanted to examine a large meatus, orifice, or incision, or different areas of such a meatus, orifice, or incision simultaneously, rather than a particular area of such meatus, orifice, or incision, resulting in an operator having to use multiple prior art illuminating means or multiple prior art examination devices. It is the object of the present invention to provide an examination instrument with multiple, independently directable light sources.

According to the invention, an acrylooptic examination device includes an examination head, a handle supporting the examination head, and first and second light sources.

According to the illustrated embodiments of the invention, the first and second light sources are independently directable. The first source is fixed with respect to the examination head and the second source is movably mounted relative to the head.

Briefly, the invention comprises an examination head, illustratively constructed partially from some light-transmissive material, such as an acrylic-styrene mixture. The examination head is mounted on a handle for manipulation of the head by an operator. The first light source is fixed in position relative to the head such that manipulation of the handle aims the light from the first light source. The second source, which is movably mounted from the handle, is independently aimed.

Illustratively, the means for coupling the examination head to the handle and light source unit includes a groove provided on the head portion of the handle and light source unit and a member on the examination head that can be inserted into said groove where it is retained such that the acrylooptic portion of said examination head is aligned with the first light source.

Further, according to the illustrative embodiments of the invention, the second light source is movably mounted vertically above the first light source.

Further, according to the present invention, separate control means are provided in the handle for using the first and second light sources independently or in combination.

The invention may be best understood by reference to the following description and accompanying drawings which illustrate the invention. In the drawings:

FIG. 2 is a partly fragmentary side elevational view of a device constructed according to the invention; and FIG. 3 is a sectional view taken generally along lines 3—3 of FIG. 2 of a detail of the embodiment of FIG. 2.

Figure 1:
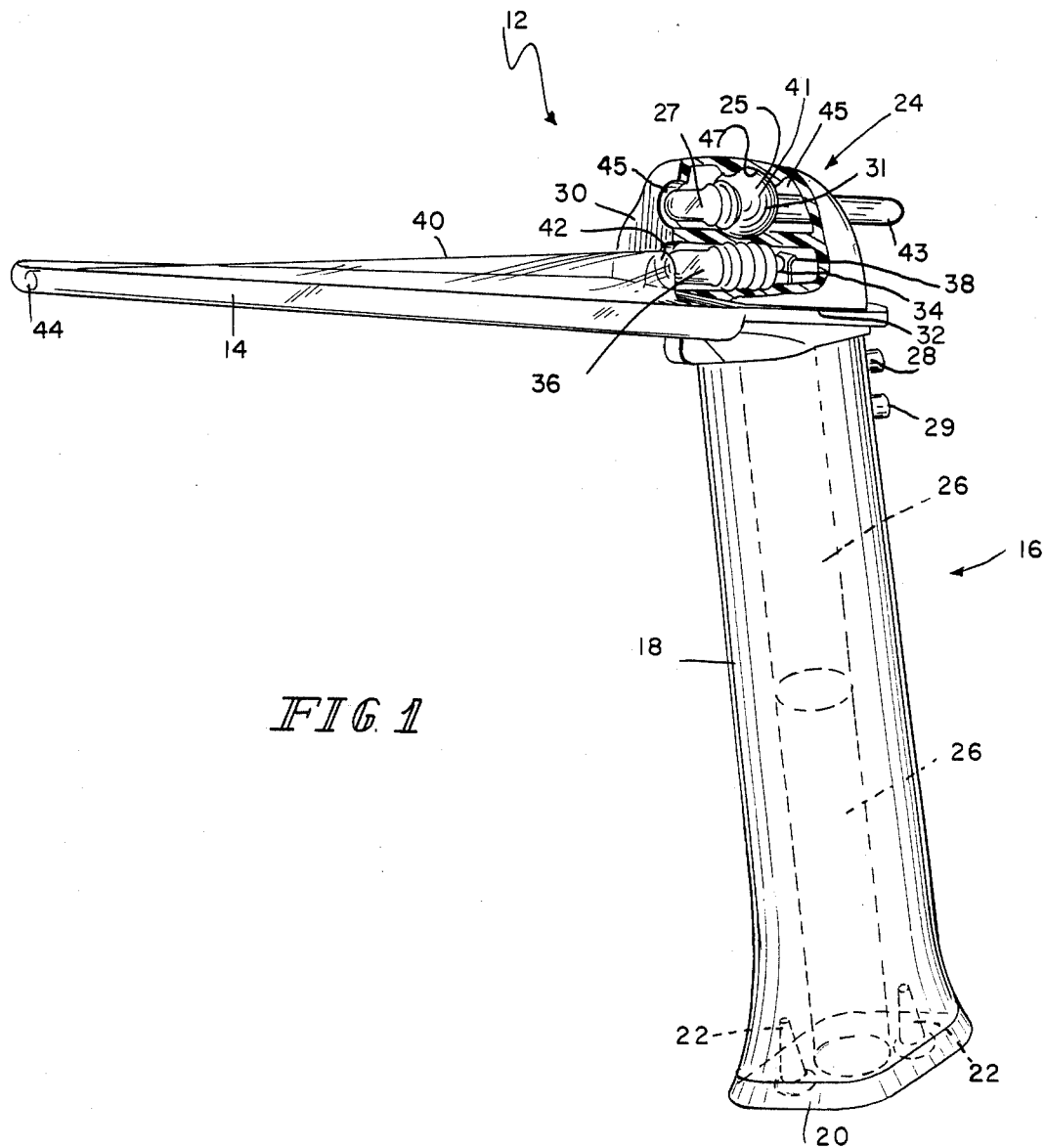
FIG. 1 is a perspective view of an acrylooptic examination device constructed according to the present invention.

Referring particularly to FIG. 1, the examination device 12 includes an examination head 14 and a base 16 which can be grasped by a physician to manipulate the examination head 14. The examination head 14 includes a member for contacting the surface of a body orifice, incision or meatus to be examined. The examination head 14 can be molded in one piece from a moderately flexible, resilient plastic material which is also highly light-transmissive. Certain acrylic-styrene mixtures are suitable.

The base 16 has a somewhat pistol grip-shaped handle 18, a bottom cap 20 held on by screws 22, and a head portion 24. The handle 18 serves to hold one or more batteries 26 which provide a power source. When an alkaline battery is used, the battery can be molded into the handle 18. Such a handle 18 may have a shelf life of up to five (5) years and a useful life of up to six (6) months. Switches 28, 29 control delivery of power from the battery.

The head portion 24 is provided with a forward face 30 and with grooves 32 which extend longitudinally along both sides of the head portion 24. Head portion 24 is provided with a first socket 34 which receives an electric light bulb 36. Conductors 38, which are illustratively molded into the plastic material from which the head portion 24 is formed, supply power through switch 28 from the battery to first bulb 36. Head portion 24 provides a second socket 25 which is vertically above socket 34. Socket 25 receives an electric light bulb 27. Conductors 31, which illustratively are molded into the plastic material from which head 24 is formed, supply power through switch 29 from the battery to bulb 27. Electrical socket 25 is movably mounted relative to the head portion 24 such that the field illuminated by bulb 27 can be adjusted relative to the field of illumination supplied by the acrylooptic portion of the examination head 14 which receives light from the first bulb 36. In this embodiment, socket 25 is provided by a member 41 formed to include a generally spherical-shaped portion movably positioned in a region of the head 24 having a complementary spherical surface 47. A lever 43 extends from the rear of member 41 and protrudes through an opening 45 in the head 24. As lever 43 is manipulated, the light bulb 27 moves relative to the stationary light bulb 36, altering the field of illumination of bulb 36. The spherical surfaces can also be in the shape of oblate or prolate spheroidal surfaces, which would provide rotation about one axis only, e.g. vertical or horizontal movement only of the bulb 27 in the head portion 24.

In this embodiment, a tongue depressor head 14 is illustrated but it is to be appreciated that a variety of other examination head configurations, such as a speculum or other surgical appliance can be utilized in conjunction with the handle 18. The bulbs 36, 27 can be used independently or in combination, dependent upon need, by turning on or off switches 28 and 29. During an examination, an operator frequently will want to concentrate attention upon one particular area and would thus use only bulb 36 in conjunction with the examination head 14 to achieve a narrow field of illumination. The examination head 14 includes a light guide 40 having a light-receiving optical portion 42 which receives light from bulb 36 and directs it towards a light-emitting surface 44 which permits transmission of light rays transmitted through the light guide 40 that exceed a critical angle. The majority of light that enters the guide 40 exits through surface 44. The light that is emitted surface 44 is somewhat directional rather than scattered, and thus can be directed toward a narrow field being examined by the operator.

In other types of examinations, it is sometimes necessary for the operator to have a somewhat larger field or even a different field illuminated. In such instances, the pivotally mounted bulb 27 is utilized to illuminate a field other than the field illuminated by bulb 36 by manipulation of lever 43. Thus an operator is able to direct light where needed to provide adequate illumination for satisfactory examination.

Referring to FIG. 2, another embodiment of the examination device made in accordance with the present invention is shown. The examination device 50 includes an examination head 54 and a base 56 which can be grasped by a physician to manipulate the examination head 54. The examination head 54 includes a member for contacting the surface of a body orifice, incision or meatus to be examined. The base 56 has a somewhat pistol grip-shaped handle 58, a bottom cap 60 held on by screws 62, and a head portion 64. The handle 58 holds batteries which provide a power source. Switch 68 controls delivery of power from the batteries. The head portion 64 is provided with forward face 70 and grooves 72 which extend longitudinally along both sides of head portion 64. Head portion 64 is provided with a first socket 75 which receives an electric light bulb 76. Conductors 78, which illustratively are molded into the plastic material from which head 64 is formed, supply power through switch 68 from the batteries to bulb 76. A second bulb 77, also controlled by switch 68, is movably mounted in a socket 82. In this embodiment contact is provided by a thumbwheel 79 which is rotatably mounted within head portion 64. The head portion 64 is provided with an aperture 84 on its top surface 86 through which a portion of the thumbwheel 79 entends to provide operator access for rotation of thumbwheel 79. As thumbwheel 79 is rotated, the bulb 77 pivots about its somewhat spherically shaped front surface 88 which is captured in a complementarily spherically shaped aperture 90 provided through the forward face 70 of head portion 64, thus permitting the field of illumination of said bulb 77 to be varied selectively. The bulbs 76, 77 can be used independently or in combination, dependent upon need, because switch 68 is a multiple position switch which controls the delivery of power to either one or both of the bulbs 76, 77.

FIG. 3 shows thumbwheel 79 with socket 82 mounted therein. It can be seen that by turning the thumbwheel 79 about its axis 92, the orientation of the bulb 77 and thus the field of illumination are varied as needed.

The examination device of the present invention thus provides a means for varying the field of illumination required during an examination operation as needed.

What is claimed is:

1. A medical examination device comprising an examination head, a base unit having a handle portion and a head portion, a first stationary light source mounted in the head portion for providing light around the examination head, a second light source, and means for movably mounting the second light source in the head portion, the examination head including a portion constructed from an optical wave-guiding material cooperatively aligned with said first light source, such that light from said first light source is directed through said optical wave-guiding portion of said examination head.

2. The examination device of claim 1 including means for independently illuminating said first light source and said second light source.

3. The examination device of claim 1 wherein the second light source is pivotally mounted within said head portion.

4. The examination device of claim 1 wherein the second light source is pivotally mounted above said first light source.

5. A medical examination device comprising an examination head, a base unit having a handle portion and a head portion, a first stationary light source mounted in the head portion for providing light around the examination head, a second light source, and means for movably mounting the second light source in the head portion, the second light source being pivotally mounted within said head portion, and the means for pivotally mounting said second light source including a light source socket member having a somewhat spherical-shaped portion pivotally engaging a region of the head portion having a complementary spherical surface.

6. A medical examination device comprising an examination head, a base unit having a handle portion and a head portion, a first stationary light source mounted in the head portion for providing light around the examination head, a second light source, and means for movably mounting the second light source in the head portion, the second light source being pivotally mounted within said head portion, and the means for pivotally mounting said second light source including a light source socket, means providing an aperture in the front of the head, a light bulb for providing light and a thumbwheel mounted for rotation in the head portion, the light bulb mounted in the socket, the light bulb including a somewhat spherical shaped surface, and the aperture-defining means including means providing a complementary, somewhat spherical shaped surface for movable engagement with the bulb's somewhat spherical shaped surface and the bulb and socket captured between the aperture and the thumbwheel, rotation of the thumbwheel changing the orientation of the bulb in the aperture.

7. A medical examination device comprising an examination head, a base unit having a handle portion and a head portion, a first stationary light source mounted in the head portion for providing light around the examination head, a second light source, and means for movably mounting the second light source in the head portion, the second light source being pivotally mounted above said first light source, and the means for pivotally mounting said second light source including a light source socket member having a somewhat spherical-shaped portion pivotally engaging a region of the head portion having complementary spherical surfaces.

8. A medical examination device comprising an examination head, a base unit having a handle portion and a head portion, a first stationary light source mounted in the head portion for providing light around the examination head, a second light source, and means for movably mounting the second light source in the head portion, the second light source being pivotally mounted above said first light source, and the means for pivotally mounting said second light source includes a light source socket, means providing an aperture in the front of the head, a light bulb for providing light and a thumbwheel mounted for rotation in the head portion, the light bulb mounted in the socket, the light bulb including a somewhat spherical shaped surface, and the aperture-defining means including means providing a complementary somewhat spherical shaped surface for movable engagement with the bulb's somewhat spherical shaped surface and the bulb and socket captured between the aperture and the thumbwheel, rotation of the thumbwheel changing the orientation of the bulb in the aperture.

* * * * *

UNITED STATES PATENT AND TRADEMARK OFFICE
CERTIFICATE OF CORRECTION

PATENT NO. : 4,566,439
DATED : January 28, 1986
INVENTOR(S) : Kermit H. Burgin

It is certified that error appears in the above-identified patent and that said Letters Patent is hereby corrected as shown below:

At column 1, line 12, delete "3,644,330" and insert therefor --3,664,330--; and

At column 1, line 14, delete "3,131,691" and insert therefor --3,131,690--.

Signed and Sealed this

Tenth Day of June 1986

[SEAL]

Attest:

DONALD J. QUIGG

Attesting Officer

Commissioner of Patents and Trademarks